United States Patent [19]
Brooks et al.

[11] Patent Number: 4,945,211
[45] Date of Patent: Jul. 31, 1990

[54] APPARATUS FOR MONITORING TEMPERATURE DEPENDENT CHANGES

[75] Inventors: John F. Brooks, Billericay; Paul L. Farnese, Southend-on-Sea, both of England

[73] Assignee: Electrothermal Engineering, Essex, England

[21] Appl. No.: 227,144

[22] Filed: Aug. 2, 1988

Related U.S. Application Data

[63] Continuation of Ser. No. 871,519, Jun. 6, 1986, Pat. No. 4,808,796.

[30] Foreign Application Priority Data

Jun. 7, 1985 [GB] United Kingdom ............... 8514384

[51] Int. Cl.⁵ .................................................. H05B 3/70
[52] U.S. Cl. ..................................... 219/385; 219/521
[58] Field of Search ............... 219/385, 386, 521, 200, 219/201, 209, 242, 428

[56] References Cited

U.S. PATENT DOCUMENTS

| | | | |
|---|---|---|---|
| 2,299,401 | 10/1942 | Melton | 219/428 |
| 2,487,161 | 11/1949 | Melton | 219/521 |
| 3,441,652 | 4/1969 | Eicker | 219/390 |
| 3,607,134 | 9/1971 | McIntyre | 219/521 |
| 3,766,360 | 10/1973 | Eddleman | 219/521 |
| 3,983,363 | 9/1976 | Alter | 219/386 |
| 4,307,288 | 12/1981 | Stine | 219/521 |
| 4,459,472 | 7/1984 | Morris | 219/521 |

Primary Examiner—Teresa J. Walberg
Attorney, Agent, or Firm—Spensley, Horn, Jubas & Lubitz

[57] ABSTRACT

Apparatus for monitoring temperature dependent changes has a heating arrangement, which includes two pieces of heat insulation material defining a cavity containing a heat sink member and an electrical heater for the heat sink member. The block is perforated to allow entry of a smaple tube and to provide a viewing passage. The arrangement is detachably mounted on a neck portion upstanding from a base.

1 Claim, 5 Drawing Sheets

APPARATUS FOR MONITORING TEMPERATURE DEPENDENT CHANGES

This is a continuation of application Ser. No. 06/871,519, now U.S. Pat. No. 4,808,796 filed on June 6, 1986.

BACKGROUND OF THE INVENTION

This invention relates to apparatus for monitoring temperature dependent changes and is specifically applicable to melting point determining apparatus. Such apparatus conventionally comprises a heating arrangement, or oven, for heating solids within a transparent sample tube up to a temperature of, for example, 350° C. Internal illumination is provided to allow the melting process to be seen through a lens. Temperature measuring means are provided to give a display of temperature which display may be held, by means of a switch, when the melting point is seen. Such apparatus could equally monitor other physical and/or chemical changes such as sublimation and viscosity changes.

Various aspects of the present invention are intended to improve such apparatus, for example by reducing its casing temperature, simplifying its internal structure and making it more convenient to operate.

SUMMARY OF THE INVENTION

According to one aspect of the present invention, there is provided a monitoring apparatus comprising a heating arrangement for heating a substance to be monitored, the heating arrangement comprising a block of heat insulating material containing within it a cavity containing a heat sink member and electrical heating means for said member, the member and block being perforated to provide an insertion passage for the insertion of a sample tube of a substance to be heated.

In the case of an embodiment in which a melting or other process is to be observed by the user, the block and member are additionally perforated to provide a viewing passage intersecting the insertion passage. In that case, the block preferably contains a recess communicating with said cavity for the passage of light from a light source onto a sample tube when disposed in the insertion passage. A focusable lens means is preferably provided for magnified viewing along said viewing passage.

Temperature detecting means are preferably mounted within the heat sink member.

The thermal mass of the heat sink member is preferably made relatively small to provide for relatively low heat supply and a low casing temperature, with a relatively rapid temperature rise. For example, the heat sink member may be made of aluminum and of a volume less than 2000 cubic millimeters, preferably less than 1500 cubic millimeters. A conventional, commercially obtainable, power resistor may supply the necessary heat in such a case. For example, a resistor of the order of 7K ohms operated by 230 volt pulses provides sufficient power for such a heat sink member. As an example, the thermal mass is sufficiently low that with a power less than 12 watts applied, the temperature of the heat sink member rises from 20° to 200° C. in less than 8 minutes, preferably less than 6 minutes, e.g. about 4 minutes.

In one embodiment of the heating arrangement, the number of parts and method of assembly are relatively simple in that the block of heat insulating material comprises fewer than four pieces, preferably only two pieces, at least one of which contains a recess such that with the two, or two of the, pieces placed together they define between them said cavity to contain the heat sink member. One of the pieces may be perforated to provide the viewing passage. The electrical heating means may be disposed in a recess in the heat sink member as may a temperature sensing member. The whole arrangement may thus be assembled without mechanical securing elements, for example without screws or bolts, as the parts of the block may be cemented or glued together. The whole heating arrangement can then simply be clamped into a suitable housing by means such as a bracket attached to the housing by one or two screws and retaining the block by pressure.

Thus, according to another aspect of the invention there is provided a heating arrangement, the arrangement comprising: a first heat insulating housing part; a second heat insulating housing part; the two parts together defining a heat insulating block within which is a cavity; a heat sink member contained within said cavity; an electrical heating element for said member also retained within said cavity; and a temperature sensing means in close thermal connection with said heat sink member, whereby the arrangement may be assembled from those five elements. As mentioned above, such an arrangement can be assembled relatively simply without any requirement for bolts or screws and at the most with bonding means for bonding the two parts of the insulating block together.

According to a further aspect of the invention, there is provided an apparatus comprising a housing incorporating a heating arrangement for heating a substance and also electrical supply and measuring means for the supply of power to the heating arrangement and for the measurement of temperature at said heating arrangement, the housing comprising a pedestal from which a neck portion is upstanding, as considered in an operative orientation of the apparatus, and the upper end of the neck portion supporting a detachable upper housing part which incorporates the heating arrangement and which is releasable from the neck portion for readily exchange with a replacement heating arrangement. By incorporating an elongate neck portion in the housing it is possible to design the heating arrangement to be at a sensible level above the user's bench and so avoid undue bending on the part of the user in use of the apparatus. Moreover, by making the upper housing part readily releasable, servicing becomes simpler in that the heating arrangement may simply be replaced should problems occur with the original heating arrangement. By using the simplified construction of heating arrangement already described, the cost of such a replacement part will be relatively low.

Platinum resistance thermometers are conventionally used for temperature sensing in such heating arrangement, but one embodiment of the present invention uses a thermocouple. Thus according to a further aspect of the invention, there is provided a temperature sensing circuit comprising a thermocouple having cold junction temperature compensating means for generating a compensating voltage to compensate for fluctuations in the thermocouple voltage with changes in its cold junction temperature, the compensating means comprising a voltage divider incorporating a resistance element the resistance of which changes with the cold junction temperature, the resistance element comprising a coil of electrically conductive wire, e.g. of copper, and with a wire diameter, e.g. less than 0.1 mm diameter, and number of turns, e.g. greater than 100, such as to provide a voltage drop which changes with cold junction temperature.

An operational amplifier may be used to combine the voltage from the divider with that of the thermocouple to provide a voltage substantially independent of cold junction temperature.

BRIEF DESCRIPTION OF THE DRAWINGS

For a better understanding of the invention and to show how the same may be carried into effect, reference will now be made, by way of example, to the accompanying drawings in which.

DESCRIPTION OF PREFERRED EMBODIMENTS

Figure 1:
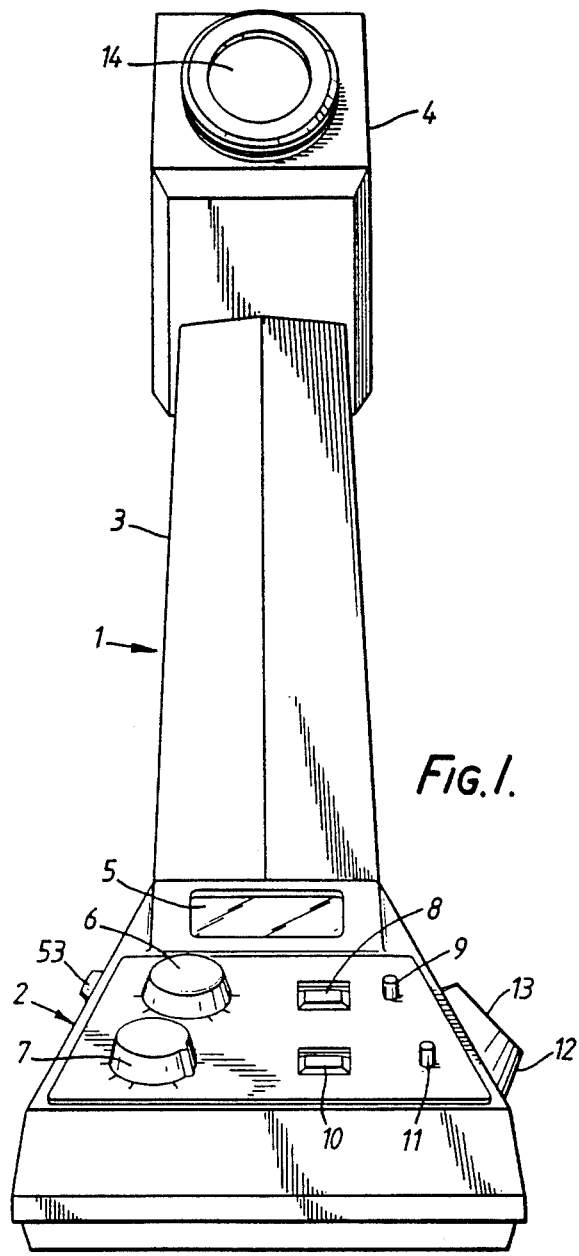
FIG. 1 is a front view of melting point determining apparatus.
Figure 7:
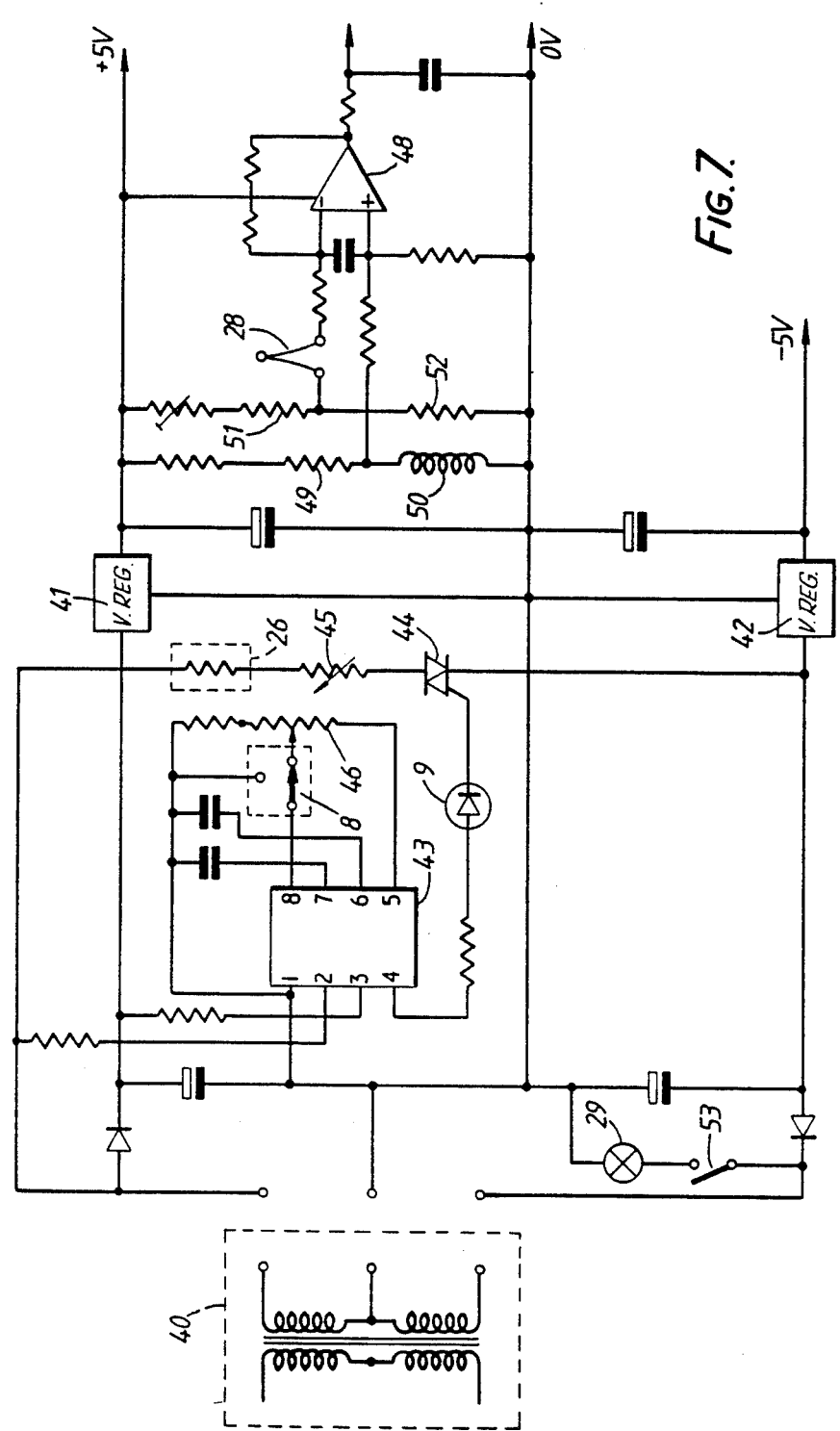
FIG. 7 is a circuit diagram of the power supply and temperature sensing arrangement of the apparatus of FIG. 1.
Figure 8:
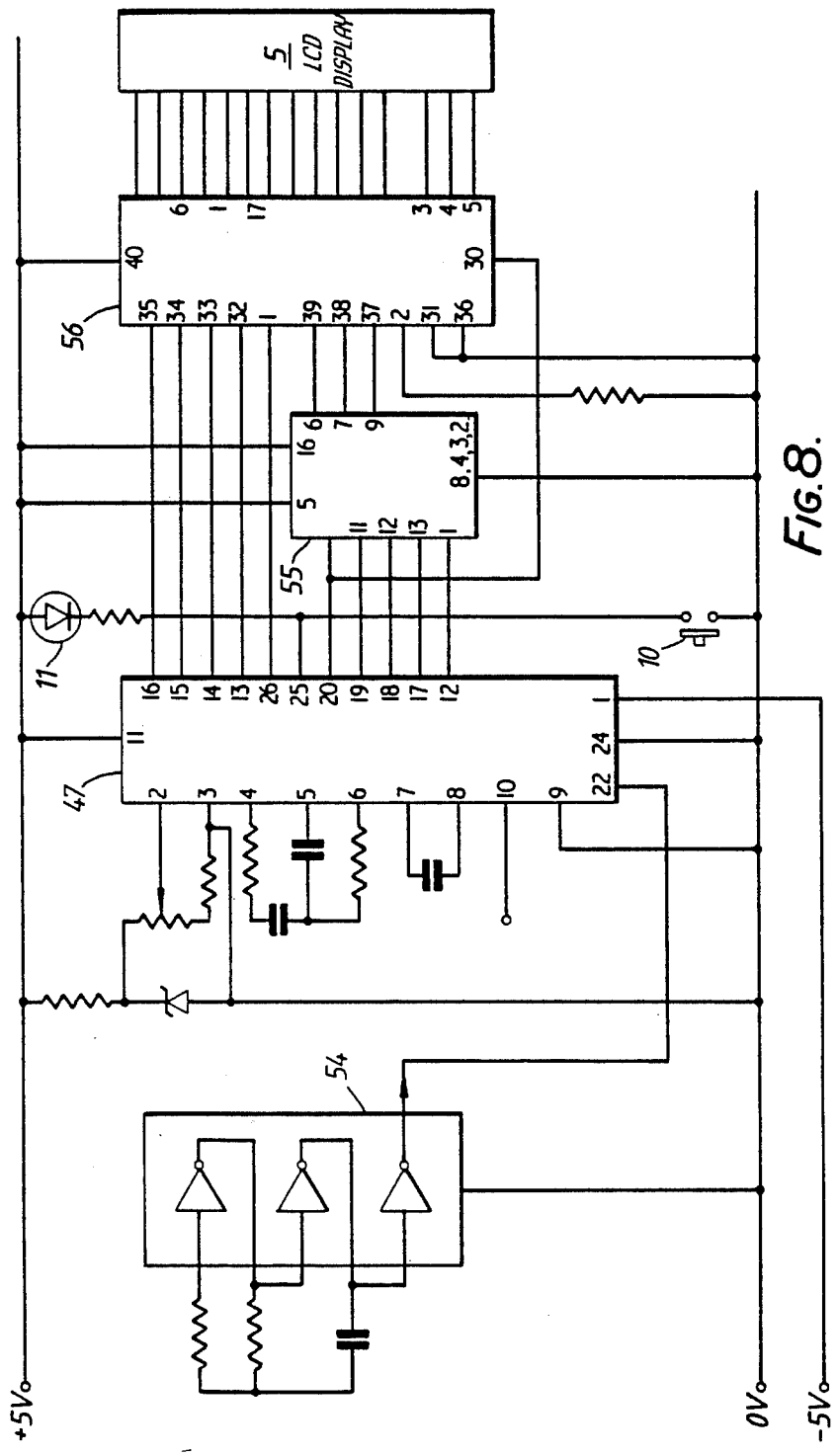
FIG. 8 is a diagram of the data display circuitry of the apparatus.

FIG. 1 is a front view of a melting point determining apparatus comprising a plastics housing generally denoted 1 which is formed from a pedestal 2, a neck portion 3 and an upper casing 4. The pedestal 2 contains power supply and temperature monitoring circuitry which is shown in FIGS. 7 and 8 and which is coupled to a temperature display 5, a coarse heating control knob 6, a fine heating control knob 7, a heating boost button 8, a heating-on indicator 9, and a display hold button 10 with its associated indicator 11.

The pedestal 2 also incorporates one or more tube holders 12 having open ends 13 for the storage, when not in use, of a plurality of sample tubes, these being conventional, capillary, transparent glass tubes to hold small crystalline samples the melting point of which is to be determined.

The neck portion 3 serves releasably to support the upper casing 4 to hold it at a sufficient height above the pedestal to enable the operator to view a heating process through a lens 14 without undue bending.

The upper casing 4 incorporates a heating arrangement or oven for heating samples contained in the aforementioned capillary tubes. Attention will now be directed to FIGS. 2 and 3 which show a cross-section and plan view of the upper casing 4 showing in particular the design of the heating arrangement in this preferred embodiment.

Figure 2:
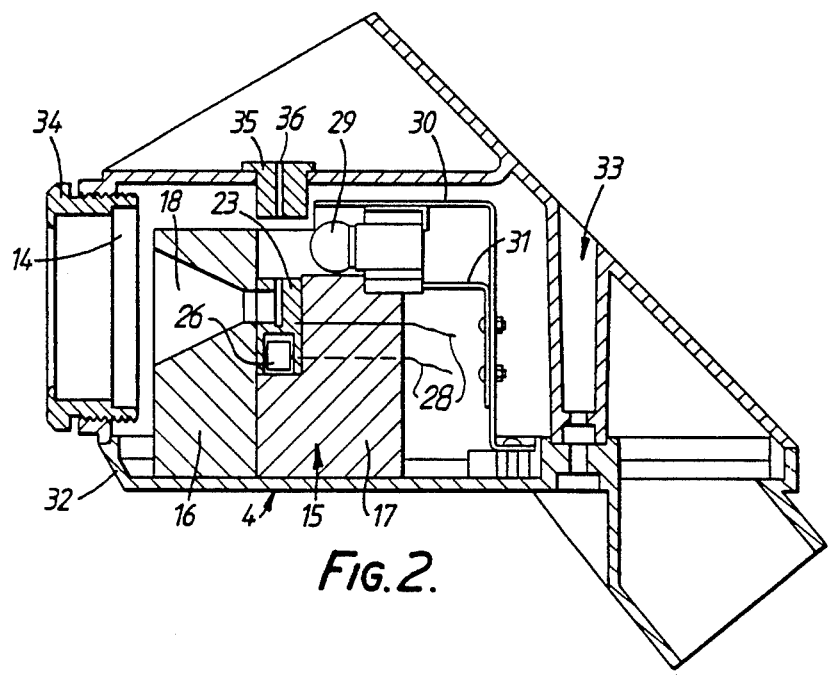
FIG. 2 is a cross-section of an upper casing of the housing of the melting point determining apparatus of FIG. 1.
Figure 3:
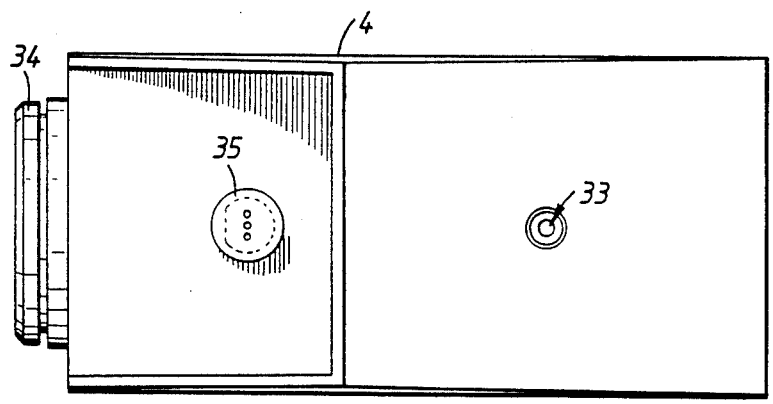
FIG. 3 is a plan view of the upper casing shown in FIG. 2.
Figure 4A:
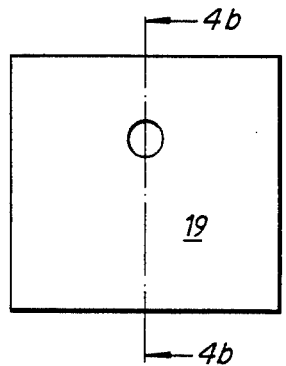
FIGS. 4A and 4B show an end and a cross-sectional view of a first moulded ceramic block.
Figure 4B:
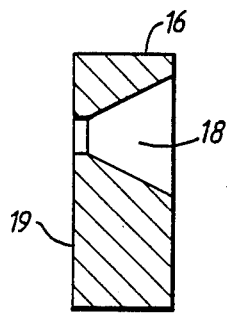
Figure 5A:
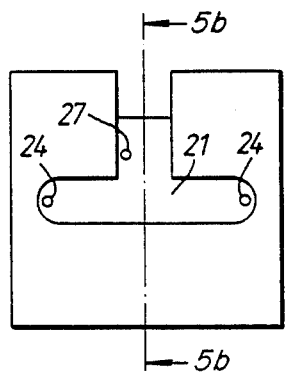
FIGS. 5A and 5B show an end and a cross sectional view of a second moulded ceramic block.
Figure 5B:
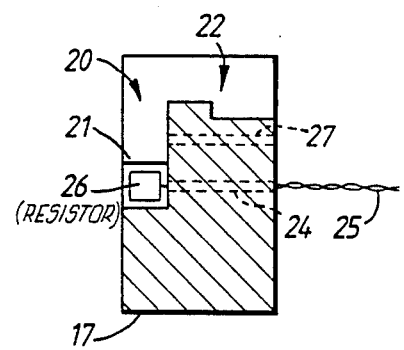

With reference to FIGS. 2 and 3, it will be seen that the casing 4 incorporates a block 15 and this block consists of two portions 16 and 17 each of formed ceramic fiber material. The block portion 16 is shown in end and cross-sectional view in FIGS. 4a and 4b, respectively, and will be seen to incorporate a tapered viewing passage 18 and a flat face 19 which is, in the assembled product, cemented to a corresponding flat face of the other block portion 17. The, block portion 17 is shown in end and cross-section view in FIGS. 5a and 5b, respectively, and will be seen to incorporate an L-shaped channel 20 having a T-shaped portion 21 and a portion 22. The portion 21 defines with the block portion 16 a cavity in which is disposed a heat sink member 23 (FIG. 2) of aluminum. This will be described in more detail hereinafter. Near the ends of the limbs of the recess portion 21 are two holes 24 through which pass the leads 25 of a commercially available power resistor 26 which acts as the heating element for the heating arrangement. The recess portion 21 includes a further hole 27 which extends through the block to provide a passage for electrical leads of a bi-metal thermocouple (NiCr-NiAl) 28 which resides within the heat sink member.

The recess portion 22 of the block portion 17 is intended to house a light source 29 shown in FIG. 2 as being supported between limbs of two brackets 30 and 31 which are riveted together and are secured to a removable base member 32 of the upper casing 4. These brackets serve no only to support the light source 29 but also apply pressure to the block 15 to retain it firmly against the base member 32. It is to be observed that the source 29 is in an upwardly open recess 22 so that any heat produced by it dissipates rapidly.

The upper casing 4 incorporates a through aperture 33 through which a bolt will pass for releasably securing this casing to the neck portion 3 of the heating apparatus.

The lens 14 is mounted in an externally threaded lens holder 34 which, by rotation, can be moved inwardly and outwardly relative to the block 15 to enable focusing to be readily attained.

A cylindrical sample insertion member 35 is incorporated in the upper part of the upper casing and contains a row of three apertures 36 aligned with three corresponding passages in the heat sink member 23 and thus acts as a guide for guiding three sample tubes during insertion into the heat sink member.

In use it will be apparent that, with one or more sample tubes inserted through member 35 and into the heat sink member 23, the source 29 may be energized to cause illumination to pass from the sample tube or tubes through the viewing passage 18 and through the lens 14 towards the user.

Figure 6A:
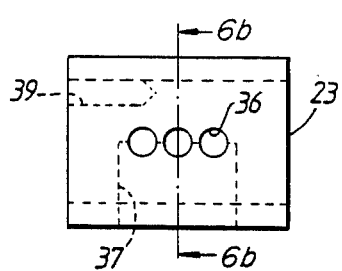
FIGS 6A and 6B show a plan and cross sectional view of a heat sink member.
Figure 6B:
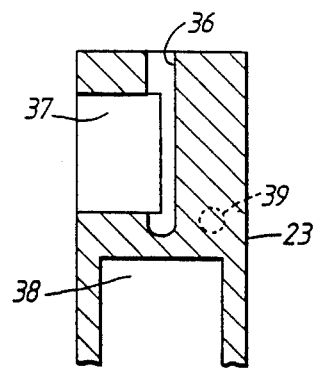

FIGS. 6a, 6b shows a plan view and cross-section of the heat sink member 23 respectively. The three passages 36, for sample tubes, intersect a recess 37 providing the end of the viewing passage 18 also defined by the block portion 16.

The heat sink member 23 also incorporates a groove 38 in which the heating element is to be disposed and a passageway 39 which is to receive the bi-metal thermocouple for use in sensing the temperature of the heat sink. The total volume of the heat sink member is a little under 1500 cubic millimeters and is manufactured of aluminum so as to have a relatively low thermal mass in order that it can be heated rapidly to a maximum temperature of about 400° C., using an electrical resistance heater 26 consisting of a conventional power resistor, e.g. of 6K8 ohms at 230V. Moreover, using such a heat sink member of relatively small size, it is possible to provide a sufficiently large mass of insulating material in the insulating block to ensure that the outer casing is maintained at a relatively low temperature during use. As an example of the thermal response of the oven, the following figures are given for full applied power of 8.5W, and with the oven commencing at 20° C.
 100° C.: 1.5 minutes
 200° C.: 4 minutes
 250° C.: 6 minutes
 350° C.: 13.5 minutes
 400° C.: 28 minutes Thus, with an applied power of less than 10W, effective temperature response is attainable with the thermal mass provided.

FIG. 7 is a circuit diagram of the power supply and temperature measuring arrangement. In FIG. 7, power supply is by way of a tapped transformer 40 of a separate, external, power supply denoted by dashed lines. The primary of the transformer is in two parts connected in series for 230 volt operation and which may be connected in parallel for 115 volt operation. The centre-tapped secondary winding of the transformer provides 24 volts output, i.e. two 12 volt supplies for two 5 volt voltage regulators 41 and 42 supplying regulated +5 volts and −5 volts for the circuit. The transformer also provides a supply to a zero voltage switch circuit 43 of the type 443. This is a zero voltage switch integrated circuit offering symmetrical burst control for a triac 44 for the pulsed control of the supply of power through two series connected resistors, 26 and 45, to the triac 44. The resistor 26 is the heating element itself and resistor 45 is an adjustable resistor coupled to knob 7 of FIG. 1 to provide fine control. Circuit 43 is coupled to a further, adjustable resistor 46 which is coupled to the knob 6 for coarse control. The gate of the triac is coupled to the circuit via a light emitting diode which constitutes the indicator 9. The switch 8 of FIG. 1 is also shown in FIG. 7 and when closed causes maximum power to be applied via the triac 44 for rapid heating of the resistor 26 and thus of the heat sink member 23. Light source 29 is shown in series with a switch 53 enabling the internal illumination to be switched off if required to eliminate heating which may be caused by this light source.

The temperature measuring circuit comprises an operational amplifier 48 supplied with signals, in opposition, from two voltage dividers 49, 50 and 51, 52, the voltage divider 51, 52 supplying its signal via the bi-metal thermocouple 28 inserted into the heat sink member in its passageway 39. The other voltage divider 49, 50 supplies a voltage to the operational amplifier in opposition to that provided by the thermocouple in order to provide for cold junction temperature compensation. For this purpose, one arm of the voltage divider 49, 50 incorporates a temperature sensitive element 50 which is placed in close proximity with the cold junction of the thermocouple 28, that cold junction being on a printed circuit board with the element 50 and mounted in the pedestal 2 remote from the heating arrangement in the upper casing 4. The compensating element 50 in this case is a compensating coil of 0.056 millimeter diameter copper wire of 196 turns and about 15 ohms resistance. The current through this coil is adjusted to give 40 micro volts per degree centigrade change and a voltage drop of 13.0 millivolts. Turning to FIG. 8, this shows the circuit diagram of the temperature display circuitry in which LCD display 5 is illustrated, driven by a display driving circuit 47 which is a 4½-digit analogue-to-digital convertor of type 7135 for use in driving multiplexed liquid crystal displays. In FIG. 8, pin numbers are indicated to show more clearly how to interconnect the elements shown therein. Circuit 47 is connected to hold switch 10, coupled between one of its pins and the +5 volt line, and also to a light emitting diode which is the indicator 11 of FIG. 1.

An inverter circuit 54 of type 4069 provides inverters interconnected to produce an oscillator providing a clock signal for circuit 47. In order to convert the BCD output of circuit 47 to binary code an 8-bit priority encoder circuit 55 of type 4532 is interposed between circuit 47 and a display driver 56 of type 7231.

In use of the apparatus, the external power supply is connected and energized in order to energize the circuits of FIGS. 7 and 8. The coarse heating control knob 6 will be set to an appropriate level to supply sufficient power to heat a sample in one or more of the passageways 36 in the heat sink member 23 approximately to its melting point and a boost switch 8 may also be actuated in order to apply full power for a short time to accelerate the heating process. When the approximately known melting point is approached, the boost switch 8 will be deactivated and the equipment allowed to heat up towards the melting point of the sample. Fine control knob 7 may be actuated to decelerate or accelerate this heating process, which will be observed through the lens 14. Advantageously, the heat applied will be reduced using the fine control knob 7 as the melting point is approached in order to minimize the rate of increase of temperature. When melting is first observed, the switch 10 may be actuated to hold the temperature display 5 at its then existing value. With experience the operator will be able to adjust the knobs 6 and 7 for a particular type of sample such that, as the melting point is approached, the temperature rise will be at the rate of less than 1 degree centigrade per minute, enabling the initial melting point to be ascertained with accuracy. It will be appreciated that melting does not occur instantaneously but over a small range of temperatures and it is possible with the present equipment visibly to distinguish two points, the first being the temperature at which melting begins and the second being the point at which the solid state within the molten sample can no longer be seen.

In a modification (not shown) of this equipment two hold switches may be provided in order to store both of these points.

Modifications and additions may be made to the apparatus as described above in order to produce embodiments with different characteristics and abilities. In one example, a connector is provided for the attachment of a printer to the apparatus in order that the hold temperature or temperatures may be printed out, possibly with the date and also with information with regard to the timing of the melting operation. In yet another form of the apparatus a printer may be built into the pedestal for automatic printing of results.

In a further modification, a microprocessor is included to provide automatic control of the apparatus, in particular to provide an automatic sequence which can be preset by the user to meet the requirements for a specific set of samples. For example, if it is required to test samples, all of which melt between 100° and 110° C. and vaporize between 180° and 190° C., the user will preset four heating ranges:
 (1) up to 100° C. rapidly
 (2) 100° to 110° C. at, say 1° C./5 minutes
 (3) 110° to 180° C. rapidly
 (4) 180° to 190° C. at, say 1° C./5 minutes This could be followed by another preset step of forced cooling.

Cooling may be achieved by a fan coupled to blow air through a plurality of tubes inserted into apertures in the blocks 15 and 16 to direct air at the heat sink member.

Such an apparatus also preferably includes means for automatically detecting changes of state so that the temperatures at which such changes occur can be recorded by the microprocessor. These means may be means detecting changes of refractive index, e g. by the use of infra-red radiation and optical fibers to direct the radiation at and to receive the radiation from the samples. At changes of state, the refractive index will change and hence so will the direction cf the radiation passing from the sample(s). An array of receiving fibers will indicate the change of direction of the radiation level changes in individual fibers of the array.

What is claimed is:

1. An improved apparatus for monitoring temperature dependent changes in a substance, the apparatus having a heating arrangement including:

a plurality of preformed pieces of heat insulating material having a first volume;

a heat sink member having a second volume, the heat sink member being insulated by the pieces of heat insulating material and being perforated to provide an insertion passage having an open end for insertion of a sample tube of a substance to be heated;

electrical heating means for heating the heat sink member;

means for monitoring a change of a substance with temperature at a position in the insertion passage spaced from the open end of the insertion passage;

temperature detecting means for detecting the temperature of the heat sink member;

means for energizing the electrical heating means to provide a first relatively slow and controlled rate of temperature change over a range of temperatures in which the change is to be monitored; and means for switching the energizing means to a relative fast rate of temperature change, whereby a substance may rapidly attain a temperature close to the range of temperature;

the improvement comprising:

the heating arrangement is a replaceable unit;

at least one of the preformed pieces includes a preformed recess, the preformed pieces mutually defining a heat insulating block containing a cavity in which the heat sink member is disposed;

the heat insulating block having an opening to provide access for a sample tube to the insertion passage; and the second volume being less than the first volume, whereby the heat sink member has a relatively low thermal mass thereby enabling the heat sink to be heated rapidly.

* * * * *